US006958416B2

(12) United States Patent
Bialer et al.

(10) Patent No.: US 6,958,416 B2
(45) Date of Patent: Oct. 25, 2005

(54) VALPROYLTAURINAMIDE DERIVATIVES AS ANTICONVULSANT AMD CNS ACTIVE AGENTS

(75) Inventors: Meir Bialer, Jerusalem (IL); Boris Yagen, Jerusalem (IL); Nina Isoherranen, Shimshon (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/482,043

(22) PCT Filed: Mar. 5, 2002

(86) PCT No.: PCT/IL02/00175

§ 371 (c)(1),
(2), (4) Date: Jul. 14, 2004

(87) PCT Pub. No.: WO03/000654

PCT Pub. Date: Jan. 3, 2003

(65) Prior Publication Data

US 2004/0242695 A1 Dec. 2, 2004

Related U.S. Application Data

(60) Provisional application No. 60/300,416, filed on Jun. 26, 2001.

(51) Int. Cl.[7] .................. C07C 307/02; A61K 31/18
(52) U.S. Cl. ................ 564/95; 564/98; 564/99; 514/601; 514/605; 514/352; 514/471; 514/419; 546/304; 548/483; 549/480
(58) Field of Search ............... 564/95, 98, 99; 514/601, 605

(56) References Cited

U.S. PATENT DOCUMENTS 4,556,673 A    12/1985  Andersen et al.
5,585,358 A    12/1996  Bialer et al.

OTHER PUBLICATIONS

S. S. Oja et al., *Anticonvulsant Activity of Some 2–Aminoethanesulphonic Acid (Taurine)Derivatives*, European Journal of Pharmacology, 1983, vol. 87, pp. 191–198.

L. Ahtee et al., *Comparison of Central nervous System Actions of Taurine and N–Plyaloyltaurine*, Acta Pharmacol. et Toxicol. 1985, vol. 57, pp. 96–105.

B. W. Collins et al/. *Plasma and Urinary Taurine in Epilepsy*, Clinical Chemistry, 1988, vol. 34, No. 4, pp. 671–675.

Meir Bialer, *Clinical Pharmacology of Valpromide*, Clin. Pharmacokinet. 1991, vol. 20, pp. 114–122.

M. Bialer et al., *Progress Report on new antiepileptic drugs: a summary of the fourth Eilat conference (EILAT VI)*, Epilepsy Research, 1999, vol. 34, pp. 1–41.

N. Isoherranen et al., *Anticonvulsant activity, teratogenicity and pharmacokinetics of novel valproyltaurinamide derivatives in mice*, British Journal of Pharmacology, 2003, vol. 139, pp. 755–764.

Primary Examiner—Shailendra Kumar
(74) Attorney, Agent, or Firm—Browdy and Neimark, PLLC

(57) ABSTRACT

The invention relates to derivatives of valproyltaurinamide of formula (I) in which $R_1$ and $R_2$ are independently hydrogen, a $C_1$–$C_6$-alkyl group, an arylalkyl group or an aryl group. The derivatives are especially useful for the treatment of epilepsy, affective illness, cognitive disorders, neurodegenerative disease, neuropathic pain syndrome, migraine, stroke, brain ischemia, or head trauma injury.

14 Claims, No Drawings

VALPROYLTAURINAMIDE DERIVATIVES AS ANTICONVULSANT AMD CNS ACTIVE AGENTS

This application claims the benefit of U.S. Ser. No. 60/300,416 filed Jun. 26, 2001.

FIELD OF THE INVENTION

The invention relates to new derivatives of valproic acid and taurine, a method for their preparation and use for thereof for the treatment of epilepsy, neurological, affective and psychotic disorders as well as for the treatment of pain and migraine.

BACKGROUND OF THE INVENTION

Four major antiepileptic drugs (AEDs) are used for the treatment of epilepsy (epileptic seizures and convulsions): phenytoin, carbamazepine, phenobarbital and valproic acid (VPA). However, about 25% of the patients do not respond to the current medications. Furthermore, AEDs are administered repetitively as chronic treatment and the adverse effects associated with antiepileptic therapy are of a major concern. All the established AEDs are associated with certain rare but severe side effects such as teratogenicity and Valproic acid itself has considerable adverse effects including the potential for fatal hepatotoxicity.

One approach to obtain improved antiepileptic agents has been to prepare the primary amide derivatives of valproic acid and its analogs (M. Bialer, Clin. Pharmacokinet., 20:114–122 (1991)). Valproyl glycinamide (M. Bialer, et al. U.S. Pat. No. 5,585,358, issued Dec. 17, 1996), is currently undergoing clinical trials in epileptic patients that are not seizure-free under the existing AEDs (M. Bialer, S. I. Johannesen, H. J. Kupferberg, R. H. Levy, P. Loiseau and E. Perucca, Epilepsy Res., 34:1–34 (1999)). Amide analogues of valproic acid have been shown to be non-teratogenic.

Taurine (2-aminoethanesulfonic acid) is an inhibitory neurotransmitter in the CNS, but its role has not yet been clearly established. Decreased taurine levels in the urine of epileptic patients and changes in the urinary taurine concentration as a consequence of antiepileptic drug therapy have been described (B. W. Colins, H. O. Goodman, C. H. Swanton and C. N. Remy, Clin. Chem., 34:671–674 (1988)). Taurine has an anticonvulsant effect when administered to the CNS, but it is clinically useless because it is unable to cross the blood brain barrier (BBB) in sufficient quantities. Certain lipophilic taurine derivatives have been disclosed in S. S. Oja, P. Kontro, I. B. Linden and G. Gothoni Eur. J. Pharmacol., 87:191–198, (1983), and L. Ahtee, H. Auvinen, A-R Maenpaa, M-L. Vahala, M. Lehtinen and J. Halmekoski, Acta Pharmacol. Toxicol., 57:96–105, (1985) and Andersen, et al., U.S. Pat. No. 4,556,673 issued Dec. 3, 1985, but these taurine derivatives have not been accepted for use in clinical practice. Certain taurine derivatives have been shown to have several CNS activities, such as effect on the pentobarbital sleeping time and locomotor activity, elevation of the cerebral dopamine concentration and antagonization of the antinociceptive effect of morphine. Taurine itself suppresses neuropathic pain in animal models. These results indicate that new taurine derivatives possess anticonvulsant activity and may have the potential to become new CNS drugs.

Based on the success of VPA and taurine in treatment of nonepileptic disorders it is expected that valproyl taurine derivative will be effective in migraine, neuropathic pain, and mania (bipolar disorders).

SUMMARY OF THE INVENTION

The present invention relates to a compound having the formula (I):

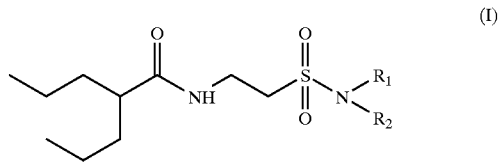

wherein $R_1$ and $R_2$ are independently the same or different and are hydrogen, a $C_1$–$C_6$ alkyl group, an arylalkyl group, or an aryl group.

The present invention also relates to a pharmaceutical composition comprising an effective amount of the compound of formula (I) as an active ingredient and any pharmaceutically acceptable carrier or diluent, for the treatment of epilepsy, neurological, affective and psychotic disorders and for the treatment of pain and migraine.

DESCRIPTION OF THE INVENTION

Compounds of particularly high activity and low toxicity result from the coupling of valproic acid with the taurine amides, and have the general structure given by formula (I) above.

In certain preferred embodiments of the present invention, the $C_1$–$C_6$ alkyl group is linear chain alkyl group. In other preferred embodiments, the $C_1$–$C_6$ alkyl group is a branched chain alkyl group. In yet other preferred embodiments, the aralkyl group is a benzyl alkylbenzyl, hydroxybenzyl alkoxybenzyl, aryloxycarbonylbenzyl nitrobenzyl, cyanobenzyl or halobenzyl group. In still other preferred embodiments, the aryl group is a phenyl, naphtyl anthracenyl, pyridinyl indolyl, furanyl, alkylphenyl, hydroxyphenyl, alkoxycarbonylphenyl, aryloxycarbonylphenyl, nitrophenyl, cyanophenyl, halophenyl group, mercaptophenyl, or aminophenyl group.

In preferred embodiments, examples of the compound having the general formula (I) according to the invention include:

N-(2-n-propylpentanoyl)taurinamide;
N-(2-n-propylpentanoyl)taurine-N'-methylamide;
N-(2-n-propylpentanoyl)taurine-N',N'-dimethylamide;
N-(2-n-propylpentanoyl)taurine-N'-ethylamide;
N-(2-n-propylpentanoyl)taurine-N'-isopropylamide;
N-(2-n-propylpentanoyl)taurine-N',N'-diethylamide;
N-(2-n-propylpentanoyl)taurine-glycinamide;

The present invention further provides a pharmaceutical composition comprising any compound hereinabove listed in a therapeutically effective amount and a pharmaceutically acceptable carrier. Preferably, the therapeutically effective amount is an amount from about 10 to about 500 mg. According to preferred embodiments of the present invention, the carrier is a solid and the composition is a tablet. According to other preferred embodiments of the present invention, the carrier is a gel and the composition is a suppository. According to yet other preferred embodiments of the present invention, the carrier is a liquid and the composition is a solution.

The present invention also relates to a method for the treatment of epilepsy, affective illness, cognitive disorders, neurodegenerative disease, neuropathic pain syndrome, migraine, stroke, brain ischemia, or head trauma injury, comprising administering to the subject in need of such treatment an amount of the compound of formula (I) effective to treat said epilepsy, affective illness, cognitive disorders, neurodegenerative disease, neuropathic pain syndrome, migraine, stroke, brain ischemia, or head trauma injury.

The compounds of general formula (I) are potent anticonvulsant agents in conventional models of human epilepsy. Several of the compounds have a surprisingly better therapeutic profile than valproic acid. Furthermore, they may also be useful in treatment of other CNS dysfunctions.

The compounds of the invention are highly effective in the MES (maximal electroshock) test and in the audiogenic seizures in genetically susceptible mice. The median effective doses ($ED_{50}$) of the agents claimed herein are considerably lower than those required to produce neurological impairment.

Therefore, results in animal models distinguish the compounds of the present invention from other antiepileptic agents and indicate that the disclosed compounds are effective against generalized and partial seizures, in addition to other forms of epilepsy.

The compounds of general formula (I) are diamides of valproic acid and may be prepared via conventional amidation processes, e.g., by reacting an activated form of the aforementioned acid with taurine of formula (II) (see diagram below), then further activating the obtained compound of formula (III) and reacting this with an amine of general formula (IV), where $R_1$ and $R_2$ are the same or different and may be a hydrogen, an al group ($C_1$–$C_6$), an arylalkyl group or aryl group or with amino acid derivative of general formula V, in which $R_1$ is the same as for the compound of formula (IV) and $R_4$ is a hydrogen or a $C_1$–$C_3$ alkyl group.

The compound of formula (III) may be prepared in a biphasic system comprised of a basic aqueous solution of the amino acid of formula (II) and a solution of valproyl chloride at a temperature between 0° and 50° C., preferably at 0°–10° C., for a period of 1 to 24 hrs, preferably 5 to 12 hrs.

The basic substance employed for the purpose is an alkali, such as sodium hydroxide, or potassium hydroxide, and said substance must be present in a quantity sufficient to neutralize the hydrochloric acid formed during the reaction.

The compound of formula (I) may be prepared from the compound of formula (III) by reacting said compound of formula (III) with $SOCl_2$ in an inert water-immiscible organic solvent, e.g. dichloromethane or tetrahydrofuran, at a temperature ranging between 25° and 70° C., preferably at 50°–60° C., for a period of 1 to 24 hrs, preferably 10 to 14 hrs. The resulting sulphonyl chloride of formula (III) may be isolated and purified, or used directly in situ. The sulphonyl chloride, whether purified or used directly, is reacted with $NHR_1R_2$ (IV), under the same conditions leading to amidation as detailed hereinabove.

The reaction of sulphonyl chloride of formula (III) with amines $NHR_1R_2$ may be carried out in an aqueous solution of the amine or in a halogenated organic solvent, such as chloroform or dichloromethane. Preferably, the solvent is water. The reaction proceeds effectively at a temperature ranging from ice-cooled to 50°–60° C., but preferably ambient temperature.

The amines of general formula (IV) are commercially available either as pure liquids or as aqueous solutions of the amine.

In the practice of the invention the amount of the compound incorporated in the pharmaceutical composition may

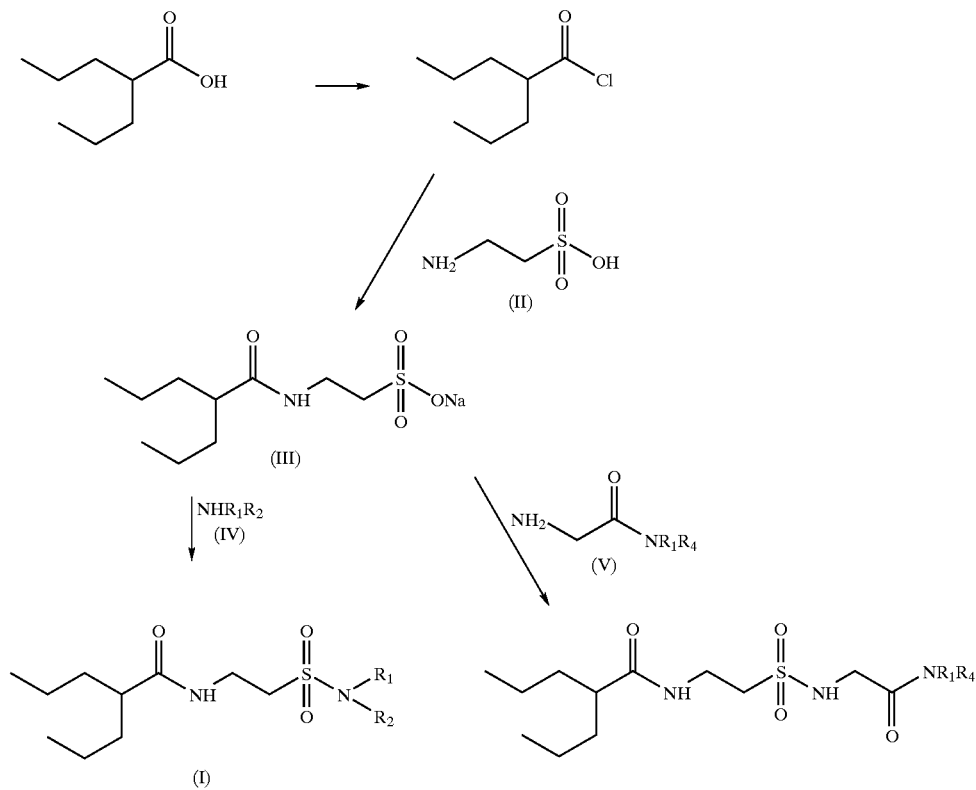

vary widely. Factors considered when determining the precise amount are well known to those skilled in the art. Examples of such factors include, but are not limited to, the subject being treated, the specific pharmaceutical carrier, and route of administration being employed and the frequency with which the composition is to be administered. A pharmaceutical composition in unit dose form for treatment of the disorders listed hereinabove preferably comprises 10 to 500 mg of the active ingredient.

In a preferred embodiment, the compound of formula (I) is administered in a pharmaceutical composition comprising the compound and a pharmaceutically acceptable carrier. As used herein, the term "pharmaceutically acceptable carrier" encompasses any of the standard pharmaceutically accepted carriers, such as a phosphate buffered saline solution, water, emulsions such as oil/water emulsion or a triglyceride emulsion, various types of wetting agents, tablets, coated tablets and capsules. An example of an acceptable triglyceride emulsion useful in the intravenous and intraperitoneal administration of the compounds is the triglyceride emulsion commercially available under the tradename Intralipid.

Typically, such carriers contain excipients such as starch, milk, sugar, certain types of clay, gelatin, stearic acid, talc, vegetable fats and oils, gums, glycols, or other known excipients. Such carriers may also include flavor and color additives or ingredients.

In the practice of the invention, the administration of the pharmaceutical composition may be effected by any of the well known methods including, but not limited to, oral, intravenous, intraperitoneal, intramuscular or subcutaneous or topical administration. Topical administration can be effected by any method commonly known to those skilled in the art and include, but are not limited to, incorporation of the pharmaceutical composition into creams, ointments, or transdermal patches.

The following experimental details are set forth to aid in an understanding of the invention, are not intended, and should not be construed, to limit in any way the invention set forth in the claims that follow thereafter.

EXAMPLE 1

N(2-n-Propylpentanoyl)taurine Na (compound of formula (III) in the diagram above)

Valproyl chloride (47.4 g, 0.29 mol) was added dropwise to an ice-cooled solution of taurine (36.5 g, 0.29 mol) and NaOH (15 g) in water (100 ml). Cooling was discontinued and the two-phase mixture was stirred at RT overnight, acidified to pH 3 with 5M HCl. The mixture was concentrated using reduced pressure and the slurry was treated with 500 ml boiling ethanol. The insoluble salts were filtered off and the product crystallized from ethanol affording 50 g (0.18 mol, 63%) of the title compound as white solid, mp 250° C.

$^1$H NMR ä ($D_2O$): 5.59 (t, 2H, NH$\underline{CH_2}$CH$_2$SO$_2$), 2.95 (t, 2H, CH$_2\underline{CH_2}$SO$_2$), 2.16 (m, 1H, pr$_2$CHCO), 1.54 (m, 4H, CH$_3$CH$_2\underline{CH_2}$), 1.31 (m, 4H, CH$_3\underline{CH_2}$CH$_2$), 0.90 (t, 6H, $\underline{CH_3}$CH$_2$CH$_2$) ppm.

IR (KBr): 3313, 3092, 2957, 2873, 1629, 1564, 1455, 1378, 1255, 1218, 1121, 1051 cm$^{-1}$

EXAMPLE 2

N(2-n-Propylpentanoyl)taurineamide

Thionyl chloride (19.6 g, 0.165 mol) was added to a solution of dry valproyl taurine (compound III) (15 g, 0.055 mol) prepared according to Ex 1, in dry CH$_2$Cl$_2$ (200 ml). The reaction mixture was stirred in 50° C. for 12 hours. The excess of CH$_2$Cl$_2$ and thionyl chloride was then distilled using reduced pressure and the residue containing the product N-(2-n-Propylpentanoyl)taurinyl chloride dissolved to 30 ml dry CH$_2$Cl$_2$. N-(2-n-Propylpentanoyl)taurinyl chloride (5.2 g, 0.018 mol) in 15 ml of dry dichloromethane was added dropwise to ice-cooled 25% aqueous ammonia (100 ml). The reaction was stirred at RT for 2 hrs. The layers were then separated and the aqueous layer extracted with EtOAc. The combined organic layers were washed succesfully with water, dried and evaporated to dryness. The residue was treated with chloroform (100 ml), and the resultant chrystals were collected by filtration washed with hexane and dried to give 4 g (0.016 mol, 89%) of the title compound as a white solid, mp 130–131° C.

Anal calc. for ($C_{12}H_{26}N_2O_3S$) C, 47.98%; H, 8.86%; N, 11.19%.

Found: C, 47.85%; H, 8.48%; N, 10.91%.

$^1$H NMR ä (CDCl$_3$, 1% TMS): 7.38 (br t, 1H, CONH), 6.25 (br s, 2H, SO$_2$NH$_2$), 3.67 (q, 2H, NH$\underline{CH_2}$CH$_2$SO$_2$), 3.24 (t, 2H, CH$_2\underline{CH_2}$SO$_2$), 2.20 (m, 1H, pr$_2$CHCO), 1.54, 1.36 (m, 4H, CH$_3$CH$_2\underline{CH_2}$), 1.30 (m, 4H, CH$_3\underline{CH_2}$CH$_2$), 0.86 (t, 6H, $\underline{CH_3}$CH$_2$CH$_2$) ppm.

IR (KBR): 3339, 3281, 3086, 2954, 2931, 2872, 1650, 1554, 1345, 1303, 1142, 930, 910 cm$^{-1}$

EXAMPLE 3

N(2-n-Propylpentanoyl)taurine-N'-methylamide

The title compound was prepared from valproyl taurine (4 g, 0.0146 mol) and aqueous N-methylamine (1.36 g, 0.0439 mol) according to the procedure described in example 2.3 g (0.0113 mol, 78%) of a white solid, mp 94° C., was thus obtained.

Anal calc. for ($C_{11}H_{24}N_2O_3S$) C, 49.96%; H, 9.17%; N, 10.60%.

Found: C, 50.25%; H, 8.84%; N, 10.47%.

$^1$H NMR ä (CDCl$_3$, 1% TMS): 6.43 (br t, 1H, CONH), 5.00 (br d, 1H, SO$_2$NH), 3.73 (q, 2H, NH$\underline{CH_2}$CH$_2$SO$_2$), 3.21 (q, 2H, CH$_2\underline{CH_2}$SO$_2$), 2.81 (d, 3H, SO$_2$NH$\underline{CH_3}$), 2.09 (m, 1H, pr$_2$CHCO), 1.57, 1.38 (m, 4H, CH$_3$CH$_2\underline{CH_2}$), 1.29 (m, 4H, CH$_3\underline{CH_2}$CH$_2$), 0.89 (t, 6H, $\underline{CH_3}$CH$_2$CH$_2$) ppm.

EXAMPLE 4

N(2-n-Propylpentanoyl)taurine-N',N'-dimethylamide

The title compound was prepared from valproyl taurine (4 g, 0.015 mol) and aqueous N-dimethylamine (1.98 g, 0.044 mol) according to the procedure described in example 2. Recrystallization from chloroform-hexane (9:1) yielded 3.1 g (0.0111 mol, 76%) of white crystals mp 135° C.

Anal calc. for ($C_{12}H_{36}N_2O_3S$): C, 51.76%; H, 9.43%; N, 10.06%.

Found: C, 51.68%; H, 9.16%; N, 10.04%.

$^1$H NMR ä (CDCl$_3$, 1% TMS): 6.21 (br t, 1H, CONH), 3.76 (q, 2H, NH$\underline{CH_2}$CH$_2$SO$_2$), 3.06 (t, 2H, NHCH$_2$ $\underline{CH_2}$SO$_2$), 2.88 (s, 6H, SO$_2$N($\underline{CH_3}$)$_2$), 209 (m, 1H, pr$_2$CHCO), 1.58, 1.40 (m, 4H, CH$_3$CH$_2\underline{CH_2}$), 1.28 (m, 4H, CH$_3\underline{CH_2}$CH$_2$), 0.88 (t, 6H, $\underline{CH_3}$CH$_2$CH$_2$) ppm.

EXAMPLE 5

N-(2-n-Propylpentanoyl)taurine-N'-isopropylamide

The title compound was prepared from valproyl taurine (g, 0.015 mol) and aqueous isopropylamine (4.43 g, 0.075 mol) according to the procedure described in example 2. A crude white solid was obtained. Recrystallization from chloroform-hexane (15:1) yielded 2.6 g (0.0089 mol, 59%) of white crystals mp 82° C.

Anal. calc. for ($C_{13}H_{28}N_2O_3S$): C, 53.39%; H, 9.65%; N, 9.58%.

Found: C, 53.09%; H, 9.35%; N, 9.54%.

$^1$H NMR ä (CDCl$_3$, 1% TMS): 6.20 (br t, 1H, CONH), 4.30 (d, 1H, SO$_2$NH), 3.68 (q, 2H, NH<u>CH</u>$_2$CH$_2$SO$_2$), 3.55 (m, 1H, SO$_2$NH<u>CH</u>CH$_3$)$_2$), 3.11 (t, 2H, <u>CH</u>$_2$SO$_2$NH), 1.99 (m, 1H, pr$_2$CHCO), 1.50, 1.34 (m, 4H, CH$_3$CH$_2$<u>CH</u>$_2$), 1.27 (m, 4H, CH$_3$<u>CH</u>$_2$CH$_2$), 1.19 (d, 6H, SO$_2$NHCH(<u>CH</u>$_3$)$_2$), 0.82 (t, 6H, <u>CH</u>$_3$CH$_2$CH$_2$) ppm.

EXAMPLE 6

N(2-n-Propylpentanoyl)taurine-N'-ethylamide

The title compound was prepared from valproyl taurine (2 g, 0.0073 mol) and aqueous ethylamine (1.32 g, 0.029 mol) according to the procedure described in example 2. A crude white solid was obtained. Recrystallization from chloroform-hexane (15:1) yielded 1.5 g (0.0054 mol, 74%) of white crystals mp 81° C.

Anal. calc. for ($C_{12}H_{26}N_2O_3S$): C, 51.77%; H, 9.41%; N, 10.06%.

Found: C, 51.54%; H, 9.14%; N, 9.78%.

$^1$H NMR ä (CDCl$_3$, 1% TMS): 6.25 (br t, 1H, CONH), 4.55 (br t, 1H, SO$_2$NH), 3.73 (q, 2H, NH<u>CH</u>$_2$CH$_2$), 3.18 (m, 4H, <u>CH</u>$_2$SO$_2$NH<u>CH</u>$_2$), 2.07 (m, 1H pr$_2$CHCO), 1.56, 1.37 (m, 4H, CH$_3$CH$_2$<u>CH</u>$_2$), 1.28 (m, 4H, CH$_3$<u>CH</u>$_2$CH$_2$), 1.24 (t, 3H, SO$_2$NHCH$_2$<u>CH</u>$_3$), 0.91 (t, 6H, <u>CH</u>$_3$CH$_2$CH$_2$) ppm.

EXAMPLE 7

N(2-n-Propylpentanoyl)taurine-N',N'-diethylamide

The title compound was prepared from valproyl taurine(2 g, 0.0073 mol) and aqueous diethylamine (1.61 g, 0.0219 mol) according to the procedure described in example 2. A crude white solid was obtained. Recrystallization from chloroform-hexane (15:1) yielded 2.0 g (0.0065 mol, 89%) of white crystals mp 88–89° C.

Anal. calc. for ($C_{14}H_{30}N_2O_3S$): C, 54.87%; H, 9.87%; N, 9.14%.

Found: C, 54.57%; H, 9.59%; N, 9.16%.

$^1$H NMR ä (CDCl$_3$, 1% TMS): 6.3 (br s, 1H CONH), 3.73 (q, 2H, NH<u>CH</u>$_2$CH$_2$SO$_2$), 328 (q, 4H, SO$_2$(<u>CH</u>$_2$CH$_3$)$_2$), 3.05 (t, 2H, CH<u>CH</u>$_2$SO$_2$), 2.07 (m, 1H, pr$_2$CHCO), 1.61, 1.38 (m, 4H, CH$_3$CH$_2$<u>CH</u>$_2$), 1.31 (m, 4H, CH$_3$<u>CH</u>$_2$CH$_2$), 1.21 (t, 6H, SO$_2$NH(CH$_2$<u>CH</u>$_3$)$_2$), 0.89 (t, 6, <u>CH</u>$_3$CH$_2$CH$_2$) ppm.

EXAMPLE 8

Biological Activity

All compounds provided herein were screened for their ability to protect against chemically and electrically induced convulsions in rats, in at least two models of epilepsy. The first model the maximal electroshock seizure test (MES), is used to show efficacy for antiepileptic agents against partial and generalized seizure type epilepsy, the common epilepsy among therapy resistant epileptic patients. The second model, the subcutaneous pentylenetetrazole test (s.c. Met) which measures seizure threshold and is a standard screening procedure to show efficacy for agents against adsence seizures. In these studies, convulsions were inhibited or prevented after oral (p.o.) and intraperitoneal (ip) administration of the compounds.

In mice the compounds were tested for their ability to protect against audiogenic seizures in the Frings audiogenic seizure susceptible mice after ip administration. This model is considered as a good screening model in pharmacologic studies for CNS active compounds.

Compounds

N-(2-Propylpentanoyl)taurinamide (hereinafter compound A), N-(2-Propylpentanoyl)taurine-N',N'-dimethylamide (hereinafter compound B) and N-(2-Propylpentanoyl)taurine-N'-isopropylamide (hereinafter compound C) N-(2-n-propylpentanoyl)taurine-N'-methylamide, N-(2-n-propylpentanoyl)taurine-N'-ethylamide and N-(2-n-propylpentanoyl)taurine-N',N'-diethylamide showed anticonvulsant activity in rats in the MES test. The $ED_{50}$ of these compounds in rats after p.o. administration in the MES model was between 40 and 250 mg/kg (Table 1). Following ip administration the ED50 values were between 40 and 60 mg/kg (Table 1) These values are eight times lower (more efficacious) than that found for VPA, and less than twice that found for phenytoin. The results are indicative of the compounds A, B and C having an efficacy against generalized seizures and complex partial seizures that evolve into generalized motor seizures.

In the audiogenic seizure susceptible mice (Frings mice) Compounds A, B and C had an ED50 between 50 and 140 mg/kg (Table 2) following ip administration. The $ED_{50}$ of compound A in this model is 3 times lower (more potent) than that of VPA. Also compounds B and C were more potent than VPA in this model. This indicates that compounds A, B and C have potential to prevent sensory induced seizures and may be useful in other CNS disorders except epilepsy. In the 6 Hz psychomotor seizure model, at stimulation intensity of 22 mA Compound A (mice ip) had an $ED_{50}$ value of 188 mg/kg.

EXAMPLE 9

Neurotoxicity

Neurotoxicity of the agents was assessed in rats (p.o. and ip administration) in the Gait and Stance test and in mice in the Rotarod Ataxia test, which assess minimal neurotoxicity. Following po administration the compounds B and C had a median neurotoxic dose of more than 200 mg/kg and compound A 500 mg/kg. The $TD_{50}$ values of compounds A, B and C were significantly higher than $TD_{50}$ for VPA (Table 1). The protective index (PI, PI=$TD_{50}/ED_{50}$) for compounds A, B and C in rats tested in the MES test following po administration was more than ten times greater than that found for VPA (Table 1). Following ip administration, the compound A had a $TD_{50}$ more than 300 mg/kg, compound B had a $TD_{50}$ of 175 mg/kg and C had a $TD_{50}$ of 627 mg/kg. These results are shown to indicate that there is a larger therapeutic dose range that can be administered before neurological side effects are usually observed.

TABLE 1

Anticonvulsant activity ($ED_{50}$) and neurotoxicity ($TD_{50}$) obtained following oral administration of N-(2-Propylpentanoyl)taurinamide (compound A), N-(2-Propylpentanoyl)taurine-N',N'-dimethylamide (compound B) and N-(2-Propylpentanoyl)taurine-N'-isopropylamide (compound C) to rats and mice in comparison to VPA.

|  | Compound A | compound B | compound C | VPA |
| --- | --- | --- | --- | --- |
| MES $ED_{50}$ (mg/kg po) | 65 | >160 | 63 | 490 |
| MES $ED_{50}$ (mg/kg ip) | 50 | 50 | 52 | — |
| sc Met $ED_{50}$ (mg/kg) | >250 | >200 | >250 | 180 |
| Andiogenic seizures | 51 | 134 | 126 | 155 |
| Neurotoxicity $TD_{50}$ (mg/kg po) | >500 | >160 | >250 | 200 |
| Neurotoxicity $TD_{50}$ (mg/kg ip) | >300 | 175 | 627 | — |
| PI (MES) ip | >7 | 3.2 | 12.1 | 0.6 (po) |

EXAMPLE 10

Pharmacokinetics

The pharmacokinetics of Compound A were evaluated in mongrel dogs. Compound A had a total body clearance (CL) of 0.11 L/h kg, Volume of distribution at steady state (Vss) of 0.84 L/kg and a half life of 5.6 h. The relatively long half-life in dogs indicates that Compound A is suitable for once or twice daily dosing. In addition, the low liver extraction ratio shows that Compound A is unlikely to be subject to a large liver first pass metabolism and consequently a high oral bioavailability can be expected for Compound A.

What is claimed is:

1. A compound having the formula:

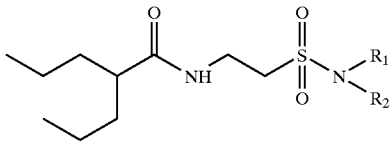

wherein $R_1$ and $R_2$ are independently the same or different and are hydrogen, a $C_1$–$C_6$ alkyl group, an arylalkyl group, or an aryl group.

2. The compound of claim 1, wherein the $C_1$–$C_6$ alkyl group is a linear chain alkyl group.

3. The compound of claim 1, wherein the $C_1$–$C_6$ alkyl group is a branched chain alkyl group.

4. The compound of claim 1, wherein the arylalkyl group is a bezyl, alkylbenzyl, hydroxybenzyl alkoxycarbonylbenzyl, aryloxycarbonylbenzyl, carboxybenzyl nitrobenzyl, cyanobenzyl, or halobenzyl group.

5. The compound of claim 1, wherein the aryl group is a phenyl, naphtyl, anthracenyl, pyridinyl, indolyl, furanyl alkylphenyl, hydroxyphenyl, alkoxycarbonylphenyl, aryloxycarbonylphenyl nitrophenyl, cyanophenyl, halophenyl group, mercaptophenyl, or aminophenyl group.

6. The compound of claim 1 selected from the group consisting of:

N-(2-n-propylpentanoyl)taurinamide;

N-(2-n-propylpentanoyl)taurine-N'-methylamide;

N-(2-n-propylpentanoyl)taurine-N',N'-dimethylamide;

N-(2-n-propylpentanoyl)taurine-N'-ethylamide;

N-(2-n-propylpentanoyl)taurine-N'-isopropylamide;

N-(2-n-propylpentanoyl)taurine-N',N'-diethylamide, and;

N-(2-n-propylpentanoyl)taurine-glycinamide.

7. The compound as defined in any one of claims 1–6, for use in the treatment of epilepsy, affective illness, cognitive disorders, neurodegenerative disease, neuropathic pain syndrome, migraine, stroke, brain ischemia, or head trauma injury.

8. A pharmaceutical composition comprising the compound defined in claim 1 in a therapeutically effective amount and a pharmaceutically acceptable carrier.

9. The pharmaceutical composition of claim 8, wherein the therapeutically effective amount is an amount from 10 to about 500 mg.

10. The pharmaceutical composition of claim 8, wherein the carrier is a solid and the composition is in the form of a tablet.

11. The pharmaceutical composition of claim 8, wherein the carrier is a gel and the composition is in the form of a suppository.

12. The pharmaceutical composition of claim 8, wherein the carrier is a liquid and the composition is in the form of a solution.

13. A method for the treatment of epilepsy, neurological, affective or psychotic disorders comprising administering to a subject in need of such treatment an amount of the compound defined in claim 1 effective to treat said epilepsy, neurological, affective or psychotic disorders.

14. A method for the treatment of bipolar disorders, chronic pain, headaches or migraines comprising administering to a subject in need of such treatment an effective amount of the compound defined in claim 1 effective to treat said bipolar disorders, chronic pain, headaches or migraines.

* * * * *